United States Patent [19]

Adachi et al.

[11] Patent Number: 5,321,041
[45] Date of Patent: Jun. 14, 1994

[54] DIPHENYLPYRROLYLFURAN DERIVATIVES

[75] Inventors: Jun Adachi; Mitsugu Ishida; Toshietsu Taniguchi; Yuichi Kato; Toshiyuki Kawagoshi; Tomoaki Tamura; Tetsuo Kadozaki; Tetsuo Miyamoto, all of Namerikawa, Japan

[73] Assignee: Nihon Iyakuhin Kogyo Co., Ltd., Toyama, Japan

[21] Appl. No.: 140,514

[22] Filed: Oct. 25, 1993

[30] Foreign Application Priority Data

Oct. 23, 1992 [JP] Japan .................. 4-286250

[51] Int. Cl.$^5$ .................. A61K 31/40; C07D 207/32; C07D 207/34
[52] U.S. Cl. .................. 514/422; 548/517
[58] Field of Search .................. 548/517; 514/422

[56] References Cited

PUBLICATIONS

CA 90 (17):136835s Phosphonamide . . . equivalents, Evans et al., p. 429, 1979.

*Primary Examiner*—Mary C. Lee
*Assistant Examiner*—Joseph K. McKane
*Attorney, Agent, or Firm*—Cushman, Darby & Cushman

[57] ABSTRACT

Diphenylpyrrolyfuran derivatives represented by the following formula (I):

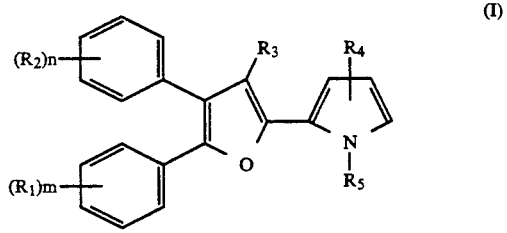

wherein $R_1$ and $R_2$ may be the same or different and independently represent a hydrogen atom, a halogen atom, a lower alkyl group, a lower alkoxy group, a lower alkylthio group, or a lower alkylsulfenyl group; m and n independently represent an integer of from 1 to 3; $R_3$ represents a hydrogen atom or a lower alkyl group, $R_4$ represents a hydrogen atom, a lower alkyl group, or a lower acyl group; and $R_5$ represents a hydrogen atom, a lower alkyl group which may have one or more suitable substituents, a lower alkoxy- or an aryloxy-carbonyl group, an acyl group, or a sufonyl group, and pharmaceutically acceptable salts thereof are disclosed. The compounds disclosed are useful as anti-inflammatory agent, anti-allergic agents, anti-platelet agents and the like.

5 Claims, No Drawings

DIPHENYLPYRROLYLFURAN DERIVATIVES

BACKGROUND OF THE INVENTION

1. Field of the Invention

The present invention relates to novel diphenylpyrrolylfuran derivatives. More specifically, the present invention relates to novel diphenylpyrrolylfuran derivatives useful as anti-inflammatory agents, anti-allergic agents, anti-platelet agents and the like.

2. Related Art

Since early 1970's, various non-steroidal anti-inflammatory agents, representative examples of such agents include indomethacin and ibuprofen, have been developed. The mechanisms of action of these drugs are mainly based on their inhibitory activities on the generation of prostaglandins by cyclooxygenases. However, these drugs selected from the view point of the inhibitory potency on the generation of prostaglandins have problems that they cannot achieve complete cure of intractable allergic and chronic inflammatory diseases [Hoshi, Iyaku Journal (Medicine and Drug Journal), 26, p. 933-937, 1990].

In general, it has been known that certain chemical mediators other than prostaglandins participate in inflammatory reactions. As such chemical mediators, bradykinin, serotonin, and complement activated products ($C_{5a}$) as well as leukotriene, interleukins and the like have been known [Nakamura, Gendai Kagaku (Chemistry Today), 217, p. 38-45, 1989, Tokyo Kagaku Dojin]. Furthermore, it has also been known that, as a result of the inflammatory reactions, active oxygens produced by wondered leukocytes may deteriorate tissue damage, and that lipid peroxides produced are strong pain-inducing substances [Yagi, Kasankashishitsu to Shikkan (Lipid peroxides and Diseases), p. 210-217 (1981), Igaku Shoin].

Accordingly, developments of drugs have been strongly desired which inhibit the generation and activities of various inflammatory mediators as well as prostaglandins together with active oxygens.

The object of the present invention is to provide novel compounds having the activities described above.

SUMMARY OF THE INVENTION

The inventors of the present invention conducted various studies to achieve the foregoing object, and as a result, they found that the compounds represented by the following formula (I) are extremely useful for preventive and therapeutic treatment of inflammatory diseases, in particular, of intractable inflammatory diseases caused by an abnormal metabolism of arachidonic acid or peroxide reaction. The present invention was achieved on the basis of these findings.

The present invention thus provides diphenylpyrrolylfuran derivatives represented by the following formula (I):

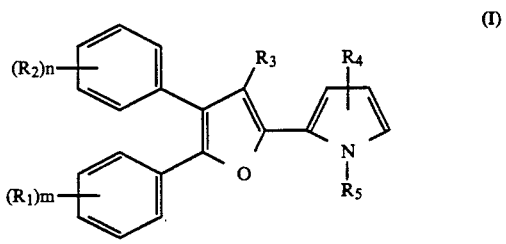

wherein $R_1$ and $R_2$ may be the same or different and independently represent a hydrogen atom, a halogen atom, a lower alkyl group, a lower alkoxy group, a lower alkylthio group, or a lower alkylsulfenyl group;

m and n independently represent an integer of from 1 to 3;

$R_3$ represents a hydrogen atom or a lower alkyl group, $R_4$ represents a hydrogen atom, a lower alkyl group, or a lower acyl group; and $R_5$ represents a hydrogen atom, a lower alkyl group which may have one or more suitable substituents, a lower alkoxy- or an aryloxy carbonyl group, an acyl group, or a sulfonyl group, and pharmaceutically acceptable salts thereof.

The present invention further provides an anti-inflammatory agent, an anti-allergic agent, and a platelet aggregation inhibiting agent comprising the compound represented by the above-described formula (I) or the pharmaceutically acceptable salt thereof as an active ingredient.

DESCRIPTION OF THE PREFERRED EMBODIMENTS

In the specification, the term "lower" means that any group or compound modified by this term have 6 or less carbon atoms, preferably, 4 or less carbon atoms. The halogen atom include a fluorine atom, a chlorine atom, a bromine atom, or an iodine atom. The alkyl group may be straight or branched and examples of the alkyl group include, for example, methyl, ethyl, propyl, isopropyl, butyl, isobutyl, sec-butyl, tertbutyl, pentyl, isoamyl and hexyl groups.

The alkoxy group and the alkylthio group are groups represented by alkyl—O—and alkyl—S—, respectively, in which the above-described alkyl group is chemically bonded with an oxygen atom or a sulfur atom. Examples of the alkoxy group include metoxy, ethoxy, propoxy, isopropoxy, butoxy, sec-butoxy and tert-butoxy groups. Examples of the alkylthio group include methylthio, ethylthio, propylthio, isopropylthio and butylthio groups.

The alkylsulfenyl group is a group represented $R_6SO$—wherein $R_6$ represents a lower alkyl group. Examples of the alkylsulfenyl group include methylsulfenyl, ethylsulfenyl, propylsulfenyl, isopropylsulfenyl and butylsulfenyl groups. The acyl group means a residue of an organic acid, and specifically, a group represented by $R_7CO$— wherein $R_7$ represents a hydrogen atom or a lower alkyl group. More specifically, examples of the acyl group include, for example, formyl, acetyl, propionyl and butylyl groups. The sulfonyl group is a group represented by $R_8SO_2$— wherein $R_8$ represents a lower alkyl or an aryl group. More specifically, examples include, for example, methanesulfonyl, benzenesulfonyl and p-toluenesulfonyl groups.

In the formula (I), where $R_5$ represents a lower alkyl group having one or more suitable substituents, such substituent on the alkyl group include a halogen atom, a hydroxy group, a lower alkoxy group, cyano group, carboxyl group, an ester group, an acyl group and the like. The alkyl group may be substituted with one or more of these substituents. Examples of the lower alkyl group having one or more substituents include, for example, trifluoromethyl, 2-chloroethyl, hydroxymethyl, 2-hydroxyethyl, 2-methoxyethyl, 2-cyanoethyl, carboxymethyl, 1-carboxyethyl, 2-carboxyethyl, 3-carboxypropyl, methoxycarbonylmethyl, ethoxycarbonylmethyl, 1-methoxycarbonylethyl, 2-methoxycarbonylethyl, 1-ethoxycarbonylethyl, 2-ethoxycarbonylethyl, 2-ethoxycarbonylpropyl, acetoxymethyl, 2-acetoxyethyl, propionyloxymethyl, 2-propionyloxyethyl, formylmethyl, 1-formylethyl, 2-formylethyl, acetonyl and 3-oxobutyl groups.

The compounds of the formula (I) may have one or more asymmetric carbon atoms in each of their molecules and various kinds of stereoisomers may exist. Pure optical isomers, mixtures of optical isomers at an arbitrary ratio, racemates, pure diastereoisomers, mixtures of diastereoisomers at an arbitrary ratio and the like fall within the scope of the present invention. Furthermore, in addition to free compounds represented by formula (I), pharmaceutically acceptable salts thereof also fall within the scope of the present invention. Examples of such salts include, for example, alkali metal salts such as sodium, potassium, calcium, and magnesium salts, and amine salts such as salts of ammonia, lower alkylamine, and alicyclic amine salts, where the compounds of the formula (I) have a carboxyl group.

According to the present invention, there are also provided compounds represented by the following formula (II) which are synthetic intermediates for the preparation of the compounds of the formula (I):

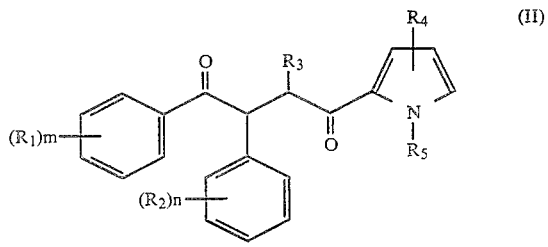

wherein $R_1$, $R_2$, $R_3$, $R_4$, $R_5$, m, and n are the same as those defined in the above-described formula (I).

For example, the diketone compounds of the formula (II):

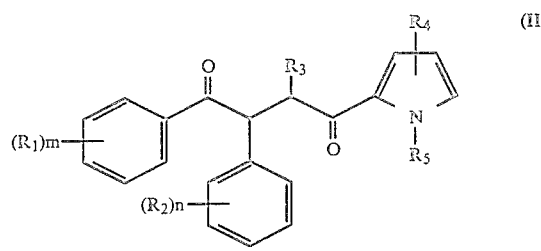

wherein $R_1$, $R_2$, $R_3$, $R_4$, $R_5$, m, and n are the same as those defined in the formula (I), can be prepared by condensing the compounds represented by the following formula (III):

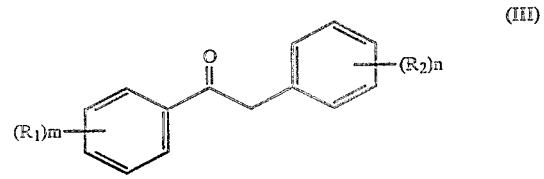

wherein $R_1$, $R_2$, m, and n are the same as those defined in the formula (I), with the compounds represented by the following formula (IV):

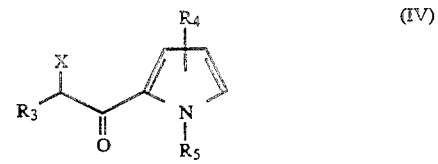

wherein $R_3$, $R_4$, and $R_5$ are the same as those defined in the formula (I) and X represents a halogen atom, in a suitable solvent in the presence of a base.

In the condensation reaction, an amount ratio of the compounds represented by the formula (Iv) to the compounds represented by the formula (III) is not particularly limited. However, it is preferable to use 1 to 5 moles, more preferably 1 to 2 moles, of the compounds of the formula (IV) for 1 mole of the compounds of the formula (III). In the reaction of the compound of formula (III) with compound of (IV), a base as a de-acid condensing agent may be used. Examples of the base include, for example, sodium carbonate, potassium carbonate, sodium hydroxide, potassium hydroxide, sodium methylate, sodium ethylate, potassium tert-butoxide and sodium hydride. These bases may generally be used in an amount of from 1 to 5 molar equivalents, preferably 1 to 2 molar equivalents, for 1 mole of the compounds of the formula (III). Examples of the reaction solvent include lower alcohols such as methanol and ethanol; ketones such as acetone and 2-butanone; aromatic hydrocarbons such as benzene, toluene and xylene; ethers such as diethyl ether and tetrahydrofuran; N,N-dimethylformamide and the like; and mixtures thereof. The reaction may generally be carried out at a temperature of from about −70° to about 100° C., preferably from −5° to 50° C.

The compounds of the formula (IV) used in the condensation reaction described above can easily be prepared by halogenating the compounds represented by the following formula (V):

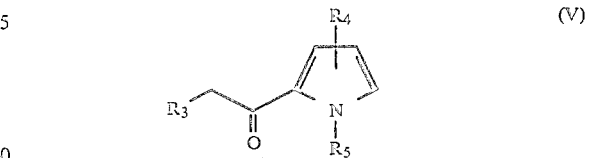

wherein $R_3$, $R_4$ and $R_5$ are the same those defined above, according to a method known to the public [for example, halogenation procedures described by Carroll et al., J. Org. Chem., 29, p. 3459, 1964; Piero et al., Synthesis, p. 212, 1990; or Shin Jikken Kagaku Koza (Experimental Chemistry, 2nd Ed.), Vol. 14, p.345, 1977, Maruzen].

The compounds of the formula (IV) can also be prepared from the pyrrole derivatives represented by the following formula (VI):

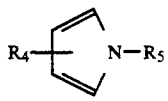

(VI)

wherein $R_4$ and $R_5$ are the same as those defined above, by a well known Vilsmeyer's reaction (for example, the method described by Piero et al., Synthesis, p. 783 (1989)) using the compounds represented by the following formula (VII):

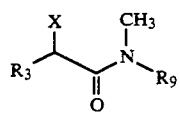

(VII)

wherein $R_3$ and X are the same as those defined above and $R_9$ represents methyl or benzyl group.

Where $R_5$ of the compounds of the formula (II) is a readily removable group, the compounds of formula (II-2) which corresponds to formula (II) wherein $R_5$ is a hydrogen atom:

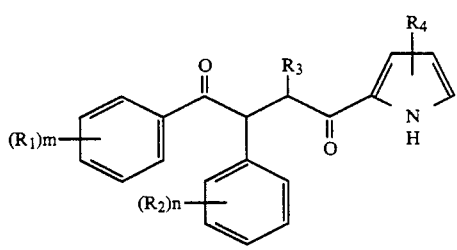

(II-2)

wherein $R_1$, $R_2$, $R_3$, $R_4$, m, and n are the same as those defined above, can be prepared by hydrolyzing the compounds of the formula (II-1):

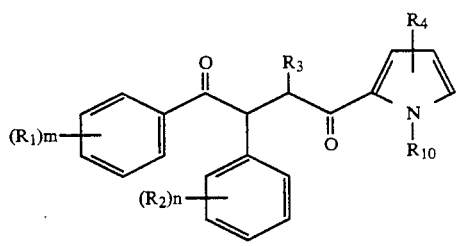

(II-1)

wherein $R_1$, $R_2$, $R_3$, $R_4$, m, and n are the same as those defined above and $R_{10}$ represents a lower alkoxy- or an aryloxy-carbonyl group, an acyl group, or a sulphonyl group. The hydrolysis reaction can be carried out according to a known method depending on the group to be removed. For example, the hydrolysis reaction can be carried out by the treatment using an acid or a base in a solvent such as water, a lower alcohol, aqueous acetone, aqueous tetrahydrofuran, aqueous dioxane or a mixture thereof at room temperature or under heating upto refluxing temperature of a solvent used.

The compounds of the following formula (II-3):

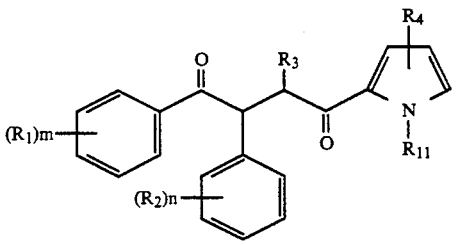

(II-3)

wherein $R_1$, $R_2$, $R_3$, $R_4$, m, and n are the same those defined above and $R_{11}$ represents a lower alkyl group which may optionally be substituted with one or more suitable substituents, can be prepared by subjecting the compounds of the formula (II-2) to an alkylation reaction.

The alkylation reaction can be carried out, for example, by reacting the compound of formula (II-2) in a suitable solvent and in the presence of a base, with an alkyl halide derivative of the formula (vIII): $X\text{-}R_{11}$ wherein $R_{11}$ is the same as that defined above and X represents a halogen atom, or with a compound of the formula (IX): $R_{12}CH=C(R_{12})R_{13}$ wherein $R_{12}$ may be the same or different and represents a hydrogen atom or a lower alkyl group and $R_{13}$ represents an acyl group, a lower alkoxycarbonyl group, an aryloxycarbonyl group, or cyano group. In the reaction, the amount of the compounds of the formula (VIII) or (IX) relative used for the compounds of the formula (II-2) is not particularly limited. However, 1 to 5 moles, preferably 1 to 2 moles of the compounds of the formula (VIII) or (IX) may generally be used for 1 mole of the compounds of the formula (II-2).

Examples of the base used for the above-described alkylation reaction include, for example, sodium hydroxide, potassium hydroxide and lithium hydroxide. These bases are generally used in an amount of from 1 to 20 moles, preferably 1 to 10 mole for 1 mole of the compounds of the formula (II-2). As the solvent, water, lower alcohols such as methanol and ethanol, ketones such as acetone and 2-butanone, aromatic hydrocarbons such as benzene, toluene and xylene, ethers such as diethyl ether and tetrahydrofuran, N,N-dimethylformamide, dimethyl sulfoxide, mixtures thereof or the like may be used. The reaction may generally be carried out at a temperature of form about $-70°$ to about $50°$ C., preferably from $-5°$ C. to room temperature. The alkylation reaction may be carried out in the presence of a reaction catalyst such as, for example, quaternary ammonium salts such as tetrabutylammonium bromide and tetrabutylammonium hydrosulfate, or crown ethers such as 18-crown-6.

It is advantageous to use the compounds of the formula (II) obtained in a manner described above, since the diphenylpyrrolyl-furan derivatives of the formula (I) can be obtained by an intramolecular dehydration reaction of the compounds of the formula (II) using a dehydrating agent.

Examples of the dehydrating agent include, for example, phosphorus oxychloride, polyphosphoric acids, polyphosphoric acid esters, phosphorus pentoxide, zinc chloride, p-toluenesulfonic acid and the like. These dehydration agents can generally be used in an amount of from 0.1 to 10 parts by weight, preferably 1 to 3 parts by weight for 1 part by weight of the compounds of the formula (II). The dehydration reaction is preferably carried out in a solvent. Examples of the solvent include aromatic hydrocarbons such as benzene, toluene and xylene and alkyl halides such as chloroform and dichloroethane. The reaction may generally be carried out under heating at a temperature of from room temperature to the reflux temperature of the solvent.

Where $R_5$ of the compounds of the formula (I) is a readily removable group, the compounds represented by the following formula (I-2) which corresponds to the compound of formula (I) wherein $R_5$ is a hydrogen atom:

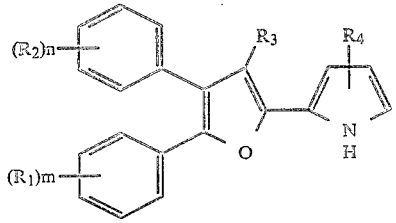
(I-2)

wherein $R_1$, $R_2$, $R_3$, $R_4$, m, and n are the same as defined above, can be prepared by hydrolysing the compound represented by the following formula (I-1):

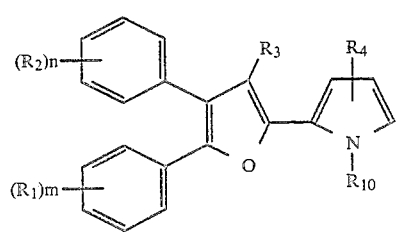
(I-1)

wherein $R_1$, $R_2$, $R_3$, $R_4$, $R_{10}$, m, and n are the same as those defined above under the same conditions as explained above about the preparation of of the compounds of formula (II-1). Furthermore, it is also possible to prepared the compounds represented by the following formula (I-3):

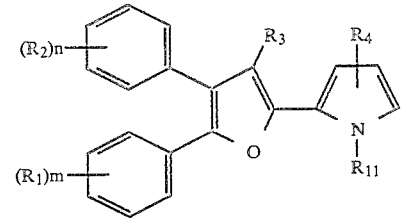
(I-3)

wherein $R_1$, $R_2$, $R_3$, $R_4$, $R_{11}$, m, and n are the same as those defined above, by alkylating the compounds of formula (I-2) under the same conditions as explained above about the alkylation of the compounds of formula (II-2).

In addition, wherein $R_4$ of the compounds of formula (I) is a hydrogen atom, the compounds represented by the following formula (I-5):

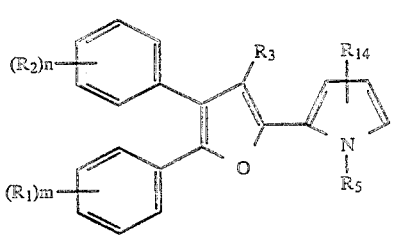
(I-5)

wherein $R_1$, $R_2$, $R_3$, $R_5$, m, and n are the same as defined above and $R_{14}$ represents an acyl group, can be prepared by subjecting the compounds represented by the following formula (I-4):

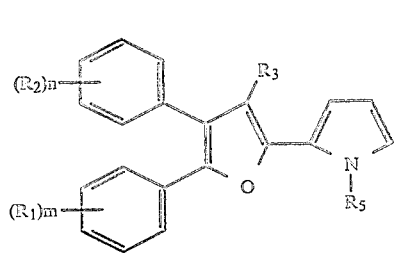
(I-4)

wherein $R_1$, $R_2$, $R_3$, $R_5$, m, and n are the same as those defined above to, for example, a Friedel-Crafts' reaction or a Vilsmeyer's reaction. The Friedel-Crafts' reaction and the Vilsmeyer's reaction can be carried out under the reaction conditions described in published documents such as, for example, Satchell et al., Chemistry Of the Carbonyl Groups, p. 233, 1966, John Wiley & Sons; Paquette, Principles of Modern Heterocyclic Chemistry, p. 115, 1968, Benjamin Inc.; and Kametani, Yuki Gousei Kagaku [Organic Synthetic Chemistry], Vol. 5, p. 182, 194, 1977, Nankodo.

The compounds represented by the following formula (1-6):

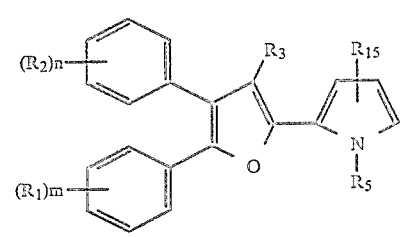
(I-6)

wherein $R_1$, $R_2$, $R_3$, $R_5$, m, and n are the same as those defined above and $R_{15}$ represents a lower alkyl group, can be prepared by reducing the compounds of formula (I-5) obtained by the aforementioned reaction, according to reactions applied for reduction of normal carbonyl groups. Examples of such reactions include, for example, Wolff-Kischner reduction, Clemmensen reduction, reduction reactions using a reducing agent such as, for example, metal hydrides such as lithium aluminum hydride and sodium boron hydride and organic boron compounds such as diborane and borane-tert-butylamine complex.

Isolation or purification of the compounds of formula (I) obtained as described above can be carried out according to known methods such as, for example, extraction, distillation, crystallization, chromatography and the like. Among the compounds of formula (1), those having a carboxyl group can be converted to the aforementioned alkali metal salts or organic amine salts according to methods known in the art.

The compounds of formula (I) of the present invention and the salts thereof are useful since they have pharmacological effects such as inhibitory activities on lipid peroxidation, cyclooxygenase, 5-lipoxygenase, carrageenin-induced paw edema, granuloma formation and platelet aggregation. The compounds of the formula (I) are particularly useful since they exhibit dual inhibition against cyclooxygenase and 5-lipoxygenase, each of them is a key enzyme in the arachidonic acid metabolic pathway. On the basis of these activities, the compounds of the present invention have restraining activities on the generation of prostaglandins and leukotrienes. The compounds are thus useful for the prevention and treatment of inflammatory diseases, in particular, of intractable inflammatory diseases, which cannot be sufficiently cured using non-steroidal anti-inflammatory agents available to date, such as chronic rheumatoid arthritis, osteoarthritis, lumbago, scapulohumeral periarthritis, cervicoomo-brachial syndrome, tendovaginitis, ankylosing spondylarthritis, acute upper respiratory tract inflammation, gout, psoriasis, ulcerative colitis, burn, symptomatic neuralgia, erythema, common cold syndrome and acute bronchitis. Furthermore, the compounds of the present invention are also useful for preventive and therapeutic treatment of other various diseases caused by an abnormal metabolism of arachidonic acid, peroxidate reaction and the like, such as bronchial asthma, atopic dermatitis, allergic rhinitis, thrombosis, cerebrovascular disease, myocardial infraction, hyperlipidemia, diabetic angiopathy, arterio sclerosis, peptic ulcer, alcoholic hepatitis, cirrhosis, fatty liver, cancer, side effects of anti-cancer agent, retinopathy, cataract, obesity, gestosis, radiation injury, shock, sepsis and various senile regressive diseases.

EXPERIMENT 1: INHIBITORY ACTIVITY ON LIPID PEROXIDATION (ANTI-OXIDATION ACTIVITY)

The captioned activity was evaluated according to the method described by Kakihana et al., Nihon Yakurigaku Zasshi (Folia Pharmacologica Japonica), 80, p. 225, 1982. To a 1 ml of a crude homogenate prepared from brain tissues of Wistar rats, 10 μl of a solution of test drug in dimethyl sulfoxide was added, and after pre-incubation under ice-cooling for 10 minutes, the mixture was subjected to a reaction at 37° C. for 30 minutes. The reaction was stopped by adding 200 μl of 35% perchloric acid to the mixture and then the mixture was centrifuged. To a 1 ml of the supernatant obtained, 0.5 ml of 0.5% thiobarbituric acid was added and the mixture was heated under a boiling water bath for 15 minutes. The mixture was cooled to room temperature and absorbance of the mixture at 532 nm was measured. The inhibitory rate was obtained using the amount of malondialdehyde generated by the solvent-treated control, which equals to 100%, and 50% median inhibitory concentration ($IC_{50}$) was calculated according to the probit method as indexes of anti-oxidation activity. The results obtained are shown in Table 1 set out below.

Hereinafter in the specification, the compound numbers of the test drugs correspond to the compound numbers in examples which follows.

TABLE 1

| Test Drug (Compound No.) | $IC_{50}$ (μM) |
|---|---|
| 117 | 4.83 |
| 165 | 2.73 |
| 175 | 3.63 |
| 176 | 4.49 |
| 178 | 3.24 |
| 184 | 3.13 |
| 185 | 2.20 |
| 188 | 2.41 |
| 217 | 2.44 |

EXPERIMENT 2: INHIBITORY ACTIVITY ON 5-LIPOXYGENASE

5-Lipoxygenase activity was determined according to the method described by Ochi et al., J. Biol. Chem.,258, p. 5754, 1983 using a crude enzyme fraction prepared from peritoneal exudated cells of guinea pigs which were induced by intraperitoneal injection of 2% case in solution. A solution of a test drug was mixed with a reaction solution (2mM ATP, 1 mM glutathione, and the enzyme fraction in 50 mM phosphate buffer, PH 7.4) and the mixture was pre-incubated at 37° C. for 5 minutes. Calcium chloride (1 mM) and 20 μM $^{14}$C-arachidonic acid were added to the mixture, and then the mixture was subjected to a reaction at 37° C. for 10 minutes. After the completion of the reaction, the product was immediately extracted, dissolved in chloroform/methanol (2:1), and developed by thin-layer chromatography. Radioactivity of the 5-hydroxyeicosatetraenoic acid (5-HETE) fraction was measured using a liquid scintillation counter. Inhibitory rate of each drug-treated group against 5-HETE generation was obtained in comparison with the solvent-treated control, and $IC_{50}$ was calculated according to the probit method. The results obtained are shown in Table 2 below.

TABLE 2

| Test Drug (Compound No.) | $IC_{50}$ (μM) |
|---|---|
| 109 | 0.85 |
| 185 | 1.00 |
| 188 | 1.11 |
| 192 | 0.91 |
| 195 | 0.91 |

EXPERIMENT 3: INHIBITORY ACTIVITY ON CYCLOOXYGENASE

Sheep seminal vesicle microsome fraction (Funakoshi) was used as an enzyme sample. A solution of a test drug was mixed with a reaction solution (3 μM epinephrine, 3 mM glutathione, and the enzyme fraction in 100 mM Tris-HCI buffer, pH 8.3). The mixture was pre-incubated at 37° C. for 5 minutes, and then 16 μ $M^{14}$C-arachidonic acid was added to the mixture, which was allowed to react for 3 minutes. After the completion of the reaction, the product was immediately extracted, dissolved in chloroform/methanol (2:1) and developed by thin-layer chromatography. Radioactivity of the prostaglandin $E_2$ ($PGE_2$) fraction was measured using a liquid scintillation counter. Inhibitory rate of each drug-treated group against $PGE_2$ generation was obtained in comparison with the solvent-treated control, and $IC_{50}$ was calculated according to the probit method. The results obtained are shown in Table 3 set out below.

TABLE 3

| Test Drug (Compound No.) | IC$_{50}$ (μM) |
| --- | --- |
| 150 | 0.082 |
| 175 | 0.069 |
| 176 | 0.111 |
| 184 | 0.075 |
| 185 | 0.095 |
| 192 | 0.057 |
| Indomethacin | 0.082 |

EXPERIMENT 4: INHIBITORY ACTIVITY ON PAW EDEMA INDUCED BY CARAGEENIN

Wistar rats (body weight: 110-130 g) starved overnight were orally administered with a test drug suspended in 0.5% CMC-Na, and after one hour, 0.1 ml of 1% carageenin solution (picnin-A, Zushi Kagaku) was subcutaneously injected into the right hind leg paw of each rat. Three hours later, the volume of the paw was determined by means of a plethysmometer (Model 7150, Ugo Basile Co.,Ltd.) and the rate of edema was evaluated in comparison with the volume of the paw before the carageenin injection as 100%. Inhibitory rate of each drug-treated group against edema formation was calculated in comparison with the solvent-treated control. The results obtained are shown in Table 4 below.

TABLE 4

| Test Drug (Compound No.) | Dose (mg/kg) | Inhibition on Edema (%) |
| --- | --- | --- |
| 109 | 10 | 49.5 |
| 117 | 10 | 50.9 |
| 142 | 10 | 45.4 |
| 175 | 10 | 44.1 |
| 192 | 10 | 38.4 |

EXPERIMENT 5: INHIBITORY ACTIVITY ON AURICLE EDEMA INDUCED BY ARACHIDONIC ACID

Evaluation was carried out using ddY mice (25-35 g) according to the method of Young et al., J. Invest. Dermatol. 82, p. 367, 1984. The mice were orally administered with a test drug suspended in 0 5% CMC-Na, and after one hour, 10 μl of arachidonic acid in acetone (50 mg/ml) were applied to front and back surfaces of the left auricles of each mouse. One hours later, the thicknesses of the left and right auricles were measured by means of a dial gauge, and the rate of edema of the left auricle was calculated in comparison with the right auricle (normal). Inhibitory rate of each drug-treated group against edema formation was calculated in comparison with the solvent-treated control. The results obtained are shown in Table 5 set out below.

TABLE 5

| Test Drug (Compound No.) | Dose (mg/kg) | Inhibition on Edema (%) |
| --- | --- | --- |
| 114 | 30 | 41.9 |
| 175 | 30 | 50.6 |
| 176 | 30 | 30.6 |
| 188 | 30 | 55.0 |
| 195 | 30 | 43.9 |
| Ibuprofen | 100 | 0 |

EXPERIMENT 6: EFFECT ON AURICLE EDEMA INDUCED BY OXAZOLONE (DELAYED ALLERGY)

Evaluation was carried out using ICR mice (27-30 g) according to the method of Seto et al., Yakugaku Zasshi (Journal of Pharmaceutical Society of Japan), 112, p. 259, 1982. The mice were sensitized by the application of 0.1 ml of 0.5% oxazolone in ethanol to shaven abdominal skin. Five days later, inflammation was induced by applying 10 μl of 0.5% oxazolone in acetone to front and back surfaces Of the right auricle. After 24 hours, the thicknesses of the left and right auricles were measured by a dial gauge, and the rate of edema of the right auricle was calculated in comparison with the left auricle (normal). A test drug was suspended in 0.5% CMC—Na and orally administered twice to each mouse , i.e., 30 minutes before and 6 hours after the inflammation-inducing treatment. Inhibitory rate of each drug-treated group against edema was calculated in comparison with the solvent-treated control. The results obtained are shown in Table 6 set out below.

TABLE 6

| Test Drug (Compound No.) | Dose (mg/kg × 2) | Inhibition on Edema (%) |
| --- | --- | --- |
| 109 | 10 | 46.8 |
| 142 | 10 | 62.2 |
| 175 | 10 | 52.1 |
| 176 | 10 | 56.4 |
| 188 | 10 | 44.2 |

EXPERIMENT 7: INHIBITORY ACTIVITY ON GRANULOMA FORMATION (PROLIFERATIVE INFLAMMATION)

Evaluation was carried out by using Wistar rats (120-140 g) according to the method described by Fujiyoshi et al., Nihon Yakurigaku Zasshi (Folia Pharmacologica Japonica), 87, p. 379, 1986. Back skin of the rat was lightly incised under anesthesia with pentobarbital, and filter paper discs for antibiotic assay (57 mg, 13.0ϕ, Whatman) sterilized by autoclave were embedded under the skin at the both axillae. 0.1 ml of a mixture of streptomycin and penicillin G (each 1 mg/ml) was administered dropwise to the incised site and the incised skin was sutured. From the day of the disc embedment, a test drug suspended in 0.5% CMC—Na was orally administered to the rat every day for 8 days. The rat was sacrificed at the day of last administration and granuloma including the filter paper was extirpated from the circumferential tissue and dried at 110° C. overnight. The dry weight of the granuloma was measured and inhibitory rate of each drug-treated group against granulation formation was calculated in comparison with the solvent-treated control. The results obtained are shown in Table 7 set out below.

TABLE 7

| Test Drug (Compound No.) | Dose (mg/kg) | Inhibition on Granuloma (%) |
| --- | --- | --- |
| 175 | 10 | 32.2 |
| 176 | 10 | 32.4 |
| 188 | 10 | 29.7 |

EXPERIMENT 8: INHIBITORY ACTIVITY ON PLATELET AGGREGATION

Blood of Japanese native white domestic rabbits was taken into a plastic centrifugal tube added with 1/10 in volume of 3.8% sodium citrate solution, and then, platelet rich plasma (PRP) containing 5 to $6 \times 10^8$/ml platelets was obtained by centrifugation for 10 minutes. under $120 \times G$. To 450 μl of the PRP, 25 μl of a solution containing the test drug (Compound 109) dissolved at a desired concentration was added. After pre-incubation at 37° C. for 3 minutes, 25 μl of an aggregatory inducer was added to the mixture and platelet aggregation was measured by means of an aggregometer (Model C450, Chronolog Co. The $IC_{50}$ against platelet aggregation induced by arachidonic acid (250 μM) and collagen (5 μg/ml) were 1.5 and 13.3 μM, respectively.

EXPERIMENT 9: ACUTE TOXICITY

Test drugs suspended in 0.5% CMC-Na were orally administered to ddY mice (22–24 g) after starving for half day, and then alive or death of the mice was observed for 2 weeks. The results obtained are shown in Table 8 set out below.

TABLE 8

| Test Drug (Compound No.) | Dose (mg/kg) | Dead Mice/ Total Mice |
| --- | --- | --- |
| 109 | 600 | 0/5 |
| 175 | 600 | 1/5 |
| 188 | 600 | 4/5 |
| 192 | 600 | 0/5 |

The foregoing results of pharmacological experiments clearly show that the compounds of the formula (I) according to the present invention have potent inhibitory activities against 5-lipoxygenase and cyclooxygenase, and that they exhibit excellent efficacy on various experimentally produced inflammation in animals. It is also apparent that they are low toxic and highly safe drugs.

The compound of the present invention represented by formula (I), per se, may be administered to patients. However, pharmaceutical compositions comprising the compounds may be formulated and administered to patients, for example, orally, parenterally (e.g., intravenous injection, intramuscular injection, and drip infusion) as well as rectally and topically for preventive or therapeutic treatments of the diseases described above. Dose of the compound of the present invention may be vary widely depending on age or weight of a patient, stage of a disease, physiological conditions, or a diagnosis by a doctor and the like. Generally, effective daily dose for an adult patient may be about 1 to 100 mg/kg weight. If desired, divided administrations for a daily dose may be carried out several times a day.

For the preparation of the pharmaceutical compositions comprising the compounds of the present invention, one or more of the compounds may be mixed with a pharmaceutically acceptable carrier, diluent, or other pharmaceutical additives, and after an addition of other pharmacologically active compounds, if necessary, the mixture may be formulated in a pharmaceutical composition in a suitable form for a route of administration. Examples of such pharmaceutical compositions include, for example, tablets, capsules, granules, liquid compositions for oral administration (syrups), injections, drip infusions, suppositories, dermatologic dosage forms (e.g., ointments, plasters) and the like.

For the preparation of pharmaceutical compositions for oral administration, compositions in the form of, for example, tablets, granules and capsules may be formulated by mixing the compounds or the salts thereof according to the present invention, together with an ordinary excipient such as lactose, glucose, corn starch and potato starch, if necessary, with a binder such as crystalline cellulose, cellulose derivatives, gum arabic, sodium alginate and gelatin; a disintegrator such as potato starch, corn starch and sodium carboxymethylcellulose; a lubricant such as talc and magnesium stearate. For the preparation of liquid compositions such as suspensions and syrups, a carrier, for example, water, saline, simple syrup, aqueous solution of dextrose, glycerin, ethanol and the like can be used. Injections may be solution or suspension of the compounds in an aqueous solvent such as distilled water for injection, saline, aqueous solutions of glucose or non-aqueous solvent such as vegetable oils, synthetic aliphatic acid glycerides, propylene glycols and the like. For the preparation of the suppositories, ordinary plasticizers and carriers such as polyalkylene glycols and aliphatic acid triglycerides can be used. These pharmaceutical composition may contain a colorant, corrigent, preservative, pH adjusting agent, buffer agent, solubilizer, isotonizing agent and the like, if necessary.

EXAMPLES

The present invention will be hereinafter explained more specifically by way of examples. However, but the present invention is not limited to these examples.

REFERENCE EXAMPLE

To a suspension of cupric bromide (43.6 g) in ethyl acetate (120 ml), a solution of 2-acetyl-1-benzenesulfonylpyrrole (23.3 g) in chloroform (120 ml) was added dropwise and the resulted mixture was heated and refluxed for 1.5 hours. Then, the reaction mixture was cooled to room temperature and filtered, and the filtrate was washed with water and dried over anhydrous magnesium sulfate. The solvent was removed by evaporation under reduced pressure and the residue was recrystallized from ethanol to give 23.9 g (78 %) of 2-bromoacetyl-1-benzenesulfonylpyrrole (Reference Compound 1). m.p. 89°–91° C.

The following compounds were obtained in the same manner as the preparation of Reference Compound 1.

2-(2-bromopropionyl)-1-benzenesulfonylpyrrole (Reference Compound 2) m.p. 71°–73° C.

2-bromoacetyl-4-ethyl-1-benzenesulfonylpyrrole (Reference Compound 3) m.p. 115°–119° C.

2-bromoacetyl-4-isopropyl-1-benzenesulfonylpyrrole (Reference Compound 4) m.p. 118°–120° C.

2-bromoacetyl-5-ethyl-1-ethoxycarbonylpyrrole (Reference Compound 5) Oily Product NMR (CDCl$_3$) δ: 1.27 (3H, t, J=7 Hz), 1.37 (3H, t, J=8 Hz), 2.77 (2H, q, J=7 Hz), 3.27 (2H, s), 3.47 (2H, q, J=8 Hz), 6.13 (1H, d, J=4 Hz), 7.07 (1H, d, J=4 Hz).

2-bromoacetyl-4-t-butyl-1-benzenesulfonylpyrrole (Reference Compound 6). m.p. 111°–115° C.

EXAMPLE 1

A solution of deoxyanisoin (12.8 g) in DMF (30 ml) was added dropwise to a suspension of sodium hydride (60% oil, 2.1 g) in N,N-dimethylformamide (DMF, 10 ml) in about 40 minutes under ice-cooling, and then the mixture was stirred for 1 hour at room temperature. The mixture was cooled to −5° C. in an ice bath and then a solution of Reference Compound 1 (17.3 g) in DMF (20 ml) was added dropwise while the temperature of the reaction mixture was kept at −5° to 10° C. The reaction mixture was stirred for 30 minutes under cooling, and then for 30 minutes at room temperature. The reaction mixture was poured into water and extracted with ethyl acetate. The extract was concentrated under reduced pressure and crystals precipitated were collected by filtration. The crystals were washed with a small amount of ethyl acetate and then with water to give 19.5 g (77.5%) of 1,2-di-(4-methoxyphenyl)-4-(1-benzenesulfonyl -2-pyrrolyl)-1,4-butanedione (Compound 1).

IR (KBr) cm$^{-1}$: 1680, 1670 (C=O).

NMR (CDCl$_3$)δ: 2.93 (1H, d. d, J=5, 16 Hz), 3.71 (3H, s), 3.80 (3H, s), 3.55 3.90 (1H, m), 5.07 (1H, d. d, J=5, 9 Hz), 6.31 (1H, t, J=4 Hz), 6.66–6.92 (4H, m), 7.02–7.57 (6H, m), 7.71–7.96 (5H, m).

m.p. 155°–157° C.

The following compounds were prepared in the same manner as the preparation of Compound 1 described above.

1-phenyl-2-(4-methoxyphenyl)-4-(1-benzenesulfonyl -4-isopropyl-2-pyrrolyl)-1,4-butanedione (Compound 2)

NMR (CDCl$_3$) δ:(only characteristic peaks are shown, the same shall apply hereinafter): 1.22 (6H, d, J=6 Hz), 2.75 (1H, m), 2.92 (1H, d. d, J=5, 16 Hz), 3.70 (3H, s), 3.60–3.90 (1H, m), 5.10 (1H, d. d, J=5, 9 Hz).

1-(4-methoxyphenyl)-2-phenyl-4-(1-benzenesulfonyl -4-isopropyl-2-pyrrolyl)-1,4-butanedione (Compound 3)

NMR (CDCl$_3$) δ: 1.21 (6H, d, J=6 Hz), 2.75 (1H, m), 2.92 (1H, d. d, J=5, 18 Hz), 3.77 (1H, d. d, J=9, 18 Hz), 3.78 (3H, s), 5.10 (1H, d. d, J=5, 9 Hz).

1,2-di-(2-methoxyphenyl)-4-(1-benzenesulfonyl -2-pyrrolyl)-1,4-butanedione (Compound 4)

NMR (CDCl$_3$) δ: 2 88 (1H, d. d, J=6, 18 Hz), 3.63 (3H, s), 3.66 (3H, s), 3.67 (1H, d. d, J=9, 18 Hz), 5.30 (1H, d. d, J=6, 9 Hz).

1,2-di-(3-methoxyphenyl)-4-(1-benzenesulfonyl -2-pyrrolyl)-1,4-butanedione (Compound 5)

NMR (CDCl$_3$) δ: 2.95 (1H, d. d, J=6, 19 Hz), 3.71 (3H, s), 3.77 (3H, s), 3.78 (1H, d. d, J=10, 18 Hz), 5.08 (1H, d. d, J=6, 10 Hz), 5.30 (1H, d. d, J=6, 9 Hz).

1,2-di-(4-methoxyphenyl)-4-(1-ethoxycarbonyl-5-ethyl-2-pyrrolyl)-1,4-butanedione (Compound 6)

NMR (CDCl$_3$) δ: 1.20 (3H, t, J=7 Hz), 1.23 (3H, t, J=Hz), 2.68 (2H, q, J=7 Hz), 3.03 (1H, d. d, J=4.5, 18 Hz), 3.70 (3H, s), 3.75 (3H, s), 3.70–4.30 (1H, m), 4.30 (2H, q, J=7 Hz), 5.20 (1H, d. d, J=4.5, 9 Hz).

1,2-di-(4-methoxyphenyl)-4-(1-benzenesulfonyl-4-ethyl-2-pyrrolyl)-1,4-butanedione (Compound 7)

NMR (CDCl$_3$) δ: 1.20 (3H, t, J=7 Hz), 2.47 (2H, q, J=7 Hz), 2.92 (1H, d. d, J=5, 17 Hz), 3.71 (3H, s), 3.79 (3H, s), 3.53–3.88 (1H, m), 5.06 (1H, d. d, J=5, 9 Hz).

1,2-di-(4-methoxyphenyl)-3-methyl-4-(1-benzenesulfonyl-2-pyrrolyl)-1,4-butanedione (Compound 8)

NMR (CDCl$_3$) δ: 0.95 (3H, d, J=7 Hz), 3.72 (3H, s), 3.78 (3H, s), 3.60–3.95 (1H, m), 4.74 (1H, d, J=10 Hz).

1-(4-methylthiophenyl)-2-(4-methoxyphenyl)-4-(1 -benzenesulfonyl-2-pyrrolyl)-1,4-butanedione (Compound 9)

NMR (CDCl$_3$) δ: 2.46 (3H, s), 2.93 (1H, d. d, J=6, 18 Hz), 3.72 (3H, s), 3.73 (1H, d. d, J=9, 18 Hz), 5.05 (1H, d. d, J=6, 9 Hz).

EXAMPLE 2

30 ml of 1N aqueous solution of sodium hydroxide was added to a suspension of Compound 1 (3.0 g) according to Example 1 in acetone (60 ml), and the mixture was heated under reflux for 16 hours with stirring. After cooling, the acetone was removed by evaporation under reduced pressure and the resulting residue was diluted with water and extracted with ethyl acetate. The extract was washed with water and dried over anhydrous magnesium sulfate. The solvent was removed by evaporation under reduced pressure to give 1.90 g (87.6%) of 1,2-di-(4-methoxyphenyl)-4-(2-pyrrolyl)-1,4-butanedione (Compound 10).

IR (KBr) cm$^{-1}$: 3280 (NH), 1670 (C=O).

NMR (CDCl$_3$) δ: 3.13 (1H, d d, J=5, 17 Hz), 3.73 (3H, s), 3.80 (3H, s), 3.92 (1H, d. d, J=9, 17), 5.18 (1H, d. d, J=5, 9 Hz), 6.20 (1H, m), 6.70–7.02 (6H, m), 7.26 (2H, d, J=9 Hz), 7.99 (2H, d, J=9 Hz), 9.40–9.88 (1H, m).

m.p. 146°–147° C.

EXAMPLE 3

Ethyl bromoacetate (0.78 g) was added at room temperature to a mixture of the compound obtained in Example 2 described above (1.40 g), 50% aqueous solution of sodium hydroxide (15 ml), tetra-n-butylammonium bromide (0.12 g), and dichloromethane (20 ml), and the mixture was stirred for 1 hour. The reaction mixture was poured into ice water and extracted with dichloromethane. The extract was washed with water and dried over anhydrous magnesium sulfate. The solvent was removed by evaporation under reduced pressure and the residue was purified by silica gel column chromatography using dichloromethane/n-hexane as an eluent to give 1.59 g (92%) of 1,2-di-(4-methoxyphenyl)-4-(1-ethoxycarbonylmethyl-2-pyrrolyl)-1,4 butanedione (Compound 11).

IR (KBr) cm$^{-1}$: 1750 (C=O).

NMR (CDCl$_3$) δ: 1.19 (3H, t, J=7 Hz), 3.10 (1H, d. d, J=5, 16 Hz), 3.73 (3H, s), 3.80 (3H, s), 3.66–3.98 (1H, m), 4.15 (2H, q,, J=7 Hz), 4.80 (1H, d, J=17 Hz), 5.14 (1H, d, J=17 Hz), 5.15 (1H, d. d, J=5, 9 Hz), 6.18 (1H, d. d, J=3, 4 Hz), 6.70–6.95 (4H, m), 7.08 (1H, d. d, J=2, 4 Hz), 7.12 (2H, d, J=9 Hz), 7.96 (2H, d, J=9 Hz).

The following compounds were prepared in the same manner as the preparation of Compound 11 described above (as NMR spectrum data, characteristic peaks are shown).

1,2-di-(4-methoxyphenyl)-4-(1-cyanomethyl-2-pyrrolyl)1,4-butanedione (Compound 12)

NMR (CDCl$_3$) δ: 3.74 (3H, s), 3.81 (3H, s), 5.05 (1H, d, J=17 Hz), 5.17 (1H, d. d, J=5, 9 Hz), 5,45 (1H, d, J=17 Hz).

1,2-di-(4-methoxyphenyl)-4-[1-(2-ethoxyethyl)-2pyrrolyl]-1,4-butanedione (Compound 13)

NMR (CDCl$_3$) δ: 1.09 (3H, t, J=7 Hz), 3.72 (3H, s), 3.79 (3H, s), 2.95–4.55 (8H, m), 5.17 (1H, d. d, J=5, 9 Hz).

1,2-di-(4methoxyphenyl)-4[1-(2ethoxycarbonylethyl)-2-pyrrolyl]-1,4-butanedione (Compound 14)

NMR (CDCl$_3$) δ: 1.18 (3H, t, J=7 Hz), 2.69 (2H, t, J=7 Hz), 3.12 (1H, d. d, J=5, 17 Hz), 3.71 (3H, s), 3.79 (3H, s), 3.60–4.18 (1H, m), 4.07 (2H, q, J=7 Hz), 4.51 (2H, t, J=7 Hz), 5.16 (1H, d. d, J=5, 9 Hz).

1,2-di-(4-methoxyphenyl)-4-(1-ethoxycarbonylmethyl-4-ethyl-2-pyrrolyl)-1,4-butanedione (Compound 15)

NMR (CDCl₃) δ: 1.16 (3H, t, J=7 Hz), 1.18 (3H, t, J=7 Hz), 2.44 (2H, q, J=7 Hz), 3.07 (1H, d. d, J=5, 17 Hz), 3.71 (3H, s), 3.79 (3H, s), 3.65–4.20 (1H, m), 4.12 (2H, q, J=7 Hz), 4.70 (1H, d, J=17 Hz), 5.07 (1H, d, J=17 Hz), 5.14 (1H, d. d, J=5, 9 Hz).

1,2-di-(4-methoxyphenyl)-4-(1-ethoxycarbonylmethyl-4-isopropyl-2-pyrrolyl)-1,4-butanedione (Compound 16)

NMR (CDCl₃) δ: 1.21 (6H, d, J=6 Hz), 1.23 (3H, t, J=7 Hz), 3.82 (3H, s), 3.90 (3H, s), 4.25 (2H, q, J=7 Hz), 4.80 (1H, d, J=17 Hz), 5.18 (1H, d, J=17 Hz).

1,2-di-(4-methoxyphenyl)-4-(1-ethoxycarbonylmethyl-5-ethyl-2-pyrrolyl)-1,4-butanedione (Compound 17)

NMR (CDCl₃) δ: 1.19 (3H, t, J=7 Hz), 1.21 (3H, t, J=8 Hz), 2.47 (2H, q, J=8 Hz), 3.69 (3H, s), 3.74 (3H, s), 4.14 (2H, q, J=7 Hz), 4.81 (1H, d, J=18 Hz), 5.20 (1H, d, J=18 Hz).

1,2-di-(4-methoxyphenyl)-4-(1-methoxycarbonylmethyl-5-ethyl-2-pyrrolyl)-1,4-butanedione (Compound 18)

NMR (CDCl₃) δ: 1.24 (3H, t, J=8 Hz), 2.48 (2H, q, J=8 Hz), 3.09 (1H, d. d, J=4.5, 18 Hz), 3.60–4.10 (1H, m), 3.69 (3H, s), 3.73 (3H, s), 3.79 (3H, s), 4.83 (1H, d, J=17 Hz), 5.24 (1H, d, J=17 Hz).

Further, using Reference Compounds 1 to 6, Compounds 19 to 45 shown in Table 9 below were prepared in the same manners as used in Examples 1 to 3.

was heated under reflux for 1.5 hours. The reaction mixture was cooled, washed with water and dried over anhydrous magnesium sulfate. The solvent was removed by evaporation under reduced pressure and the residue was purified by silica gel column chromatography using ethyl acetate/n-hexane as an eluent to give 6.5 g (84.3%) of 2,3-di-(4-methoxyphenyl)-5-(1-benzenesulfonyl-2-pyrrolyl) furan (Compound 101).

NMR (CDCl₃) δ: 3.79 (3H, s), 3 83 (3H, s), 6.34 (1H, t, J=4 Hz), 6.53 (1H, d. d, J=2, 4 Hz), 6.66 (1H, s), 6.78 (2H, d, J=9 Hz), 6.88 (2H, d, J=9 Hz), 7 19–7.81 (10H, m).

The following compounds were prepared in the same manner as the preparation of Compound 101 described above.

2,3-di-(4-methoxyphenyl)-5-(1-methyl-2-pyrrolyl)furan (Compound 102)

NMR (CDCl₃) δ: 3.72 (3H, s), 3.76 (3H, s), 3.77 (3H, s), 6.14 (1H, d. d, J=3, 4 Hz), 6.42 (1H, s), 6.48 (1H, d d, J=2, 4 Hz), 6.61 (1H, d. d, J=2, 3 Hz), 6.77 (2H, d, J=9 Hz), 6.86 (2H, d, J=9 Hz), 7,33 (2H, d, J=9 Hz), 7.47 (2H, d, J=9 Hz).

2,3-di-(4-methoxyphenyl)-5-(1-ethyl-2-pyrrolyl)furan (Compound 103)

NMR (CDCl₃) δ: 1 40 (3H, t, J=7 Hz), 3.68 (3H, s), 3.72 (3H, s), 4.12 (2H, q, J=7 Hz), 6.15 (1H, d d, J=3, 4 Hz), 6.42 (1H, s), 6.47 (1H, d. d, J=2, 4 Hz), 6.67 (1H,

TABLE 9

| Compound No. | (R₁)ₘ | (R₂)ₙ | R₃ | R₄ | R₅ | m.p. (°C.) |
|---|---|---|---|---|---|---|
| 19 | H | H | H | H | SO₂Ph | 139–141 |
| 20 | H | H | H | 4-CH(CH₃)₂ | SO₂Ph | 135–136 |
| 21 | 4-CH₃ | 4-CH₃ | H | H | SO₂Ph | 110–112 |
| 22 | 4-CH₃ | 4-OCH₃ | H | H | SO₂Ph | 132–134 |
| 23 | 4-OCH₃ | 4-CH₃ | H | H | SO₂Ph | 130–132 |
| 24 | 4-F | 4-F | H | H | SO₂Ph | 181–186 |
| 25 | 4-F | 4-OCH₃ | H | H | SO₂Ph | 140–142 |
| 26 | 4-OCH₃ | 4-F | H | H | SO₂Ph | 194–196 |
| 27 | 4-Cl | 4-OCH₃ | H | H | SO₂Ph | 129–131 |
| 28 | 4-OCH₃ | 4-Cl | H | H | SO₂Ph | 117–119 |
| 29 | 4-OCH₃ | H | H | H | SO₂Ph | 192–195 |
| 30 | 4-OCH₃ | H | H | H | H | 182–184 |
| 31 | H | 4-OCH₃ | H | H | SO₂Ph | 115–118 |
| 32 | 4-OCH₃ | 4-OCH₃ | H | H | CH₃ | 133–135 |
| 33 | 4-OCH₃ | 4-OCH₃ | H | H | C₂H₅ | 125–127 |
| 34 | 4-OCH₃ | 4-OCH₃ | H | 4-C₂H₅ | H | 168–170 |
| 35 | 4-OCH₃ | 4-OCH₃ | H | 5-C₂H₅ | H | 154–156 |
| 36 | 4-OCH₃ | 4-OCH₃ | H | 4-CH(CH₃)₂ | SO₂Ph | 145–150 |
| 37 | 4-OCH₃ | 4-OCH₃ | H | 4-CH(CH₃)₂ | H | 186–189 |
| 38 | 4-OCH₃ | 4-OCH₃ | H | 4-C(CH₃)₃ | SO₂Ph | 75–78 |
| 39 | 4-OCH₃ | 4-OC₂H₅ | H | H | SO₂Ph | 125–127 |
| 40 | 4-OC₂H₅ | 4-OCH₃ | H | H | SO₂Ph | 167–170 |
| 41 | 4-OC₂H₅ | 4-OC₂H₅ | H | H | SO₂Ph | 157–158 |
| 42 | 4-OCH₃ | 3,4-(OCH₃)₂ | H | H | SO₂Ph | 176–179 |
| 43 | 2,4-(OCH₃)₂ | 4-OCH₃ | H | H | SO₂Ph | 148–151 |
| 44 | 3,4-(OCH₃)₂ | 4-OCH₃ | H | H | SO₂Ph | 185–188 |
| 45 | 2,3,4-(OCH₃)₃ | 4-OCH₃ | H | H | SO₂Ph | 134–135 |

EXAMPLE 4

To a solution of the compound prepared in Example 1 (8.06 g) in toluene (80 ml), phosphorus oxychloride (2.4 g) was added at room temperature and the mixture d. d, J=2, 3 Hz), 6.76 (2H, d, J=9 Hz), 6.85 (2H, d, J=9 Hz), 7.33 (2H, d, J=9 Hz), 7.47 (2H, d, J=9 Hz).

EXAMPLE 5

To a solution of Compound 101 (4.90 g) obtained in Example 4 described above in methanol (50 ml), 10% aqueous solution of sodium hydroxide (6 ml) was added and the mixture was heated under reflux for 4.5 hours with stirring. After cooling, the reaction mixture was treated in the same manner as in Example 2 to give 3.33 g (95.5%) of 2,3-di-(4-methoxyphenyl)-5-(2-pyrrolyl)furan (Compound 104).

IR (KBr) cm$^{-1}$: 3400 (NH).

NMR (CDCl$_3$) δ: 3.81, (3H, s), 3.83 (3H, s), 6.27 (1H, m), 6.47 (1H, s), 6.40–6.54 (1H, m), 6.72–7.01 (5H, m), 7.34 (2H, d, J=9 Hz), 7.46 (2H, d, J=9 Hz), 8.42–8.78 (1H, br.)

m.p 110°–112° C. (ethyl ether).

EXAMPLE 6

The compound obtained in Example 5 described above (2.60 g) and ethyl bromoacetate (1.51 g) were allowed to react and treated in the same manner as Example 3 to give 2.86 g (88%) of 2,3-di-(4-methoxyphenyl)-5-(1-ethoxycarbonylmethyl-2-pyrrolyl) furan (Compound 105).

IR (KBr) cm$^{-1}$: 1750 (C=O).

NMR (CDCl$_3$) δ: 1.18 (3H, t, J=7 Hz), 3.78 (3H, s), 3.82 (3H, s), 4.18 (2H, q, J=7 Hz), 4.91 (2H, s), 6.23 (1H, d. d, J=3, 4 Hz), 6.46 (1H, s), 6.50 (1H, d. d, J=2, 4 Hz), 6.69 (1H, d. d, J=2, 3 Hz), 6.81 (2H, d, J=9 Hz), 6.88 (2H, d, J=9 Hz), 7.33 (2H, d, J=9 Hz), 7.43 (2H, d, J=9 Hz).

m.p. 82°–85° C. (ethanol/ethyl ether).

EXAMPLE 7

Phosphorus oxychloride (4.02 g) was added dropwise to a solution of N,N-dimethylacetamide (2.60 g) in dichloroethane (20 ml) under ice-cooling, and then the mixture was stirred for 1 hour at room temperature. A solution of the compound obtained in Example 5 described above (6.04 g) in dichloroethane (10 ml) was added dropwise to the reaction mixture which was again cooled on ice. The reaction mixture was stirred for 30 minutes under ice-cooling and then for 1 hour at room temperature, 10% aqueous solution of sodium hydroxide (60 ml) was added and further stirred for 3 hours. The crystals precipitated were collected by filtration, dried and recrystallized from ethyl acetate to give 5.80 g (85.6%) of 2,3-di-(4-methoxyphenyl)-5-(5-acetyl-2-pyrrolyl)furan (Compound 106).

IR (KBr) cm$^{-1}$: 3260 (NH), 1640 (C=O).

NMR (CDCl$_3$—DMSO—d$_6$) δ: 2.43 (3H, s), 3.85 (3H, s), 3.87 (3H, s), 6.58 (1H, d. d, J=3, 5 Hz), 6.90 (2H, d, J=9 Hz), 6.97 (2H, d, J=9 Hz), 7.11 (1H, s), 7.41 (2H, d, J=9 Hz), 7.61 (2H, d, J=9 Hz), 11.77 (1H, br. s).

m.p. 205°–207° C.

EXAMPLE 8

A mixture of the compound obtained in Example 7 described above (3.81 g), potassium hydroxide (1.66 g), hydrazine hydrate (1.48 g), and diethylene glycol (40 ml) was heated on an oil bath and stirred for 2 hours at 170° to 190° C. After cooling, the reaction mixture was diluted with water and extracted with ethyl ether. The extract was washed with water and dried (anhydrous magnesium sulfate). The solvent was removed by evaporation under reduced pressure and the residue was purified by column chromatography using dichloromethane/n-hexane hexane (1:1) as an eluent to give 2.90 g (79.1%) of 2,3-di-(4-methoxyphenyl)-5-(5-ethyl-2-pyrrolyl)furan (Compound 107)

IR (KBr) cm$^{-1}$: 3350 (NH).

NMR (CDCl$_3$) δ: 1.22 (3H, t, J=7 Hz), 2.60 (2H, q, J=7 Hz), 3.72 (3H, s), 3.74 (3H, s), 5.83–6.07 (1H, m), 6.38 (1H, s), 6.23–6.50 (1H, m), 6.82 (2H, d, J=9 Hz), 6.88 (2H, d, J=9 Hz), 7.34 (2H, d, J=9 Hz), 7.52 (2H, d, J=9 Hz) 8.45 (1H, br. s).

EXAMPLE 9

A solution of the compound obtained in Example 8 above (2.70 g) in DMF (50 ml) was ice-cooled, and potassium t-butoxide (0.85 g) was added to the solution. After stirring for 1 hour at room temperature, a solution of methyl bromoacetate (1.16 g) in DMF (5 ml) was added dropwise to the reaction solution. The resulted mixture was stirred for 30 minutes at room temperature, and then diluted with water and extracted with ethyl acetate. The extract was treated in an ordinary manner to give 2.06 g (64.1%) of 2,3-di-(4-methoxyphenyl)-5-(1-methoxycarbonylmethyl-5-ethyl-2-pyrrolyl) furan (Compound 108).

IR (KBr) cm$^{-1}$: 1760 (C=O).

NMR (CDCl$_3$) δ: 1.28 (3H, t, J=7 Hz), 2.56 (2H, q, J=7 Hz), 3.74 (3H, s), 3.79 (3H, s), 3.82 (3H, s), 4.86 (2H, s), 6.01 (1H, d, J=4 Hz), 6.42 (1H, s), 6.44 (1H, d, J=4 Hz), 6.81 (2H, d, J=9 Hz), 6.88 (2H, d, J=9 Hz), 7.34 (2H, d, J=9 Hz), 7.42 (2H, d, J=9 Hz).

m.p. 108°–110° C. (ethanol/ethyl ether).

EXAMPLE 10

Aqueous solution of sodium hydroxide (10%, 3.2 ml) was added to a solution of the compound obtained in Example 9 described above (1.80 g) in DMF (15 ml) and the mixture was stirred for 2 hours at room temperature. The reaction mixture was poured into ice water, acidified with diluted hydrochloric acid and extracted with ethyl acetate. The extract was treated in an ordinary manner to give 1.49 g (85.5%) of 2,3-di-(4-methoxyphenyl)-5-(1-carboxymethyl-5-ethyl-2-pyrrolyl)furan (Compound 109).

IR (KBr) cm$^{-1}$: 3400–2400, 1730 (COOH).

NMR (CDCl$_3$) δ: 1.28 (3H, t, J=7 Hz), 2.55 (2H, q, J=7 Hz), 3.71(3H, s), 3.82 (3H, s), 4.91 (2H, s), 6.02 (1H, d, J=4 Hz), 6.42 (1H, s), 6.44 (1H, d, J=4 Hz), 6.70 (2H, d, J=9 Hz), 6.86 (2H, d, J=9 Hz), 7.27 (2H, d, J=9 Hz), 7.34 (2H, d, J=9 Hz), 8.40 (1H, br. s).

m.p. 203°–205° C. (ethyl acetate/n-hexane).

EXAMPLE 11

Lithium aluminum hydride (0.09 g) was added under ice-cooling to a solution of the compound obtained in Example 6 described above (1.08 g) in anhydrous tetrahydrofuran (20 ml), and the mixture was stirred for 1 hour. Water and then diluted hydrochloric acid were added to the reaction mixture, and the mixture was extracted with ethyl acetate. The extract was treated in an ordinary manner to give 0.96 g (98.5%) of 2,3-di-(4-methoxyphenyl)-5-[1-(2-hydroxyethyl-2-pyrrolyl]furan (Compound 110).

IR (neat) cm$^{-1}$: 3600–3200 (OH).

NMR (CDCl$_3$) δ: 1.70 (1H, br. peak), 3.79 (3H, s), 3.83 (3H, s) 3.94 (2H, t, J=5 Hz), 4.31 (2H, t, J=5 Hz), 6.20 (1H, d. d, J=3, 4 Hz ), 6.47 (1H, s), 6.40–6.54 (1H, m), 6.71–6.98 (5H, m), 7.33 (2H, d, J=9 Hz), 7.44 (2H, d, J=9 Hz).

EXAMPLE 12

A solution of acetyl chloride (0.18 g) in dichloromethane (5 ml) was added to a solution of the compound obtained in Example 11 described above (0.80 g) and pyridine (0.18 g) in dichloromethane (15 ml), and the mixture was stirred for 2 hours at room temperature. The reaction mixture was washed with water and dried over anhydrous magnesium sulfate. The solvent was removed by evaporation under reduced pressure and the residue was recrystallized from ethyl ether/n-hexane to give 0 67 g (75 6%) of 2,3-di-(4-methoxyphenyl)-5-[1-(2-acetoxyethyl-2-pyrrolyl]furan (Compound 111).

IR (KBr) cm$^{-1}$: 1735 (C=O).

NMR (CDCl$_3$) δ: 2.01 (3H, s), 3.80 (3H, s), 3.83 (3H, s), 4.42 (4H, s), 6.20 (1H, t, J=4 Hz), 6.46 (1H, m), 6.49 (1H, s), 6.66–7.03 (5H, m), 7.34 (2H, d, J=9 Hz), 7.46 (2H, d, J=9 Hz).

m.p. 78°–79° C.

Compounds 112 to 221 shown in Table 10 below were prepared in the same manners as described in Examples 4 to 12 above.

TABLE 10

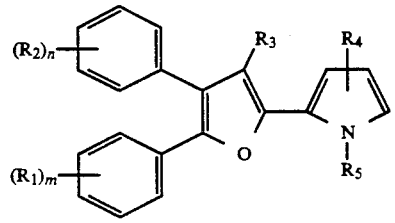

(I)

| Comp. No. | (R$_1$)$_m$ | (R$_2$)$_n$ | R$_3$ | R$_4$ | R$_5$ | m.p. (°C.) |
|---|---|---|---|---|---|---|
| 112 | H | H | H | H | SO$_2$Ph | 132–133 |
| 113 | H | H | H | H | CH$_2$CO$_2$Et | 69–70 |
| 114 | H | H | H | H | CH$_2$CO$_2$H | 153–154 |
| 115 | H | H | H | 4-CH(CH$_3$)$_2$ | SO$_2$Ph | 125–127 |
| 116 | H | H | H | 4-CH(CH$_3$)$_2$ | CH$_2$CO$_2$Et | 118–119 |
| 117 | H | H | H | 4-CH(CH$_3$)$_2$ | CH$_2$CO$_2$H | 158–160 |
| 118 | H | H | H | 5-CH$_3$ | CH$_2$CO$_2$Et | 106–109 |
| 119 | H | H | H | 5-CH$_3$ | CH$_2$CO$_2$H | 206–209 |
| 120 | H | H | H | 5-C$_2$H$_5$ | CH$_2$CO$_2$Et | 64–66 |
| 121 | H | H | H | 5-C$_2$H$_5$ | CH$_2$CO$_2$H | 186–190 |
| 122 | H | H | H | 5-CHO | H | 169–171 |
| 123 | H | H | H | 5-COCH$_3$ | H | 223–225 |
| 124 | 4-F | 4-F | H | H | SO$_2$Ph | 111–112 |
| 125 | 4-F | 4-F | H | H | CH$_2$CO$_2$Et | 58–59 |
| 126 | 4-F | 4-F | H | H | CH$_2$CO$_2$H | 172–174 |
| 127 | 4-CH$_3$ | 4-CH$_3$ | H | H | CH$_2$CO$_2$H | 201–204 |
| 128 | 4-CH$_3$ | 4-CH$_3$ | H | 5-CH$_3$ | CH$_2$CO$_2$Et | 90–92 |
| 129 | 4-CH$_3$ | 4-CH$_3$ | H | 5-CH$_3$ | CH$_2$CO$_2$H | 217–219 |
| 130 | 4-CH$_3$ | 4-CH$_3$ | H | 5-C$_2$H$_5$ | CH$_2$CO$_2$Et | 103–104 |
| 131 | 4-CH$_3$ | 4-CH$_3$ | H | 5-C$_2$H$_5$ | CH$_2$CO$_2$H | 214–216 |
| 132 | 4-CH$_3$ | 4-CH$_3$ | H | 5-CHO | H | 210–212 |
| 133 | 4-CH$_3$ | 4-CH$_3$ | H | 5-COCH$_3$ | H | 231–233 |
| 134 | H | 4-OCH$_3$ | H | H | SO$_2$Ph | 101–103 |
| 135 | H | 4-OCH$_3$ | H | H | H | 149–151 |
| 136 | H | 4-OCH$_3$ | H | H | CH$_2$CO$_2$Et | 86–88 |
| 137 | H | 4-OCH$_3$ | H | H | CH$_2$CO$_2$H | 172–174 |
| 138 | H | 4-OCH$_3$ | H | H | CH(CH$_3$)CO$_2$Et | 91–93 |
| 139 | H | 4-OCH$_3$ | H | H | CH(CH$_3$)CO$_2$H | 89–92$^{a)}$ |
| 140 | H | 4-OCH$_3$ | H | 4-CH(CH$_3$)$_2$ | SO$_2$Ph | 101–103 |
| 141 | H | 4-OCH$_3$ | H | 4-CH(CH$_3$)$_2$ | CH$_2$CO$_2$Et | 110–112 |
| 142 | H | 4-OCH$_3$ | H | 4-CH(CH$_3$)$_2$ | CH$_2$CO$_2$H | 132–135 |
| 143 | H | 4-OCH$_3$ | H | 5-CH$_3$ | CH$_2$CO$_2$Et | 79–80 |
| 144 | H | 4-OCH$_3$ | H | 5-CH$_3$ | CH$_2$CO$_2$H | 181–183 |
| 145 | H | 4-OCH$_3$ | H | 5-C$_2$H$_5$ | CH$_2$CO$_2$Et | 89–90 |
| 146 | H | 4-OCH$_3$ | H | 5-C$_2$H$_5$ | CH$_2$CO$_2$H | 168–171 |
| 147 | H | 4-OCH$_3$ | H | 5-CHO | H | 180–182 |
| 148 | H | 4-OCH$_3$ | H | 5-COCH$_3$ | H | 206–208 |
| 149 | 4-OCH$_3$ | H | H | H | CH$_2$CO$_2$Et | 76–77 |
| 150 | 4-OCH$_3$ | H | H | H | CH$_2$CO$_2$H | 197–199 |
| 151 | 4-OCH$_3$ | H | H | H | CH(CH$_3$)CO$_2$H | 138–140 |
| 152 | 4-OCH$_3$ | H | H | 4-CH(CH$_3$)$_2$ | SO$_2$Ph | 105–107 |
| 153 | 4-OCH$_3$ | H | H | 4-CH(CH$_3$)$_2$ | CH$_2$CO$_2$Et | 95–97 |
| 154 | 4-OCH$_3$ | H | H | 4-CH(CH$_3$)$_2$ | CH$_2$CO$_2$H | 179–180$^{b)}$ |
| 155 | 4-OCH$_3$ | H | H | 5-CH$_3$ | CH$_2$CO$_2$Et | 90–91 |
| 156 | 4-OCH$_3$ | H | H | 5-CH$_3$ | CH$_2$CO$_2$H | 184–186 |
| 157 | 4-OCH$_3$ | H | H | 5-C$_2$H$_5$ | H | 92–95 |
| 158 | 4-OCH$_3$ | H | H | 5-C$_2$H$_5$ | CH$_2$CO$_2$Et | 74–76 |
| 159 | 4-OCH$_3$ | H | H | 5-C$_2$H$_5$ | CH$_2$CO$_2$H | 182–185 |
| 160 | 4-OCH$_3$ | H | H | 5-CHO | H | 168–170 |
| 161 | 4-OCH$_3$ | H | H | 5-COCH$_3$ | H | 212–214 |
| 162 | 4-OCH$_3$ | 4-CH$_3$ | H | 5-C$_2$H$_5$ | CH$_2$CO$_2$H | 190–192 |
| 163 | 4-CH$_3$ | 4-OCH$_3$ | H | H | CH$_2$CO$_2$H | 199–201 |
| 164 | 4-CH$_3$ | 4-OCH$_3$ | H | 5-CH$_3$ | CH$_2$CO$_2$H | 210–213 |
| 165 | 4-CH$_3$ | 4-OCH$_3$ | H | 5-C$_2$H$_5$ | CH$_2$CO$_2$H | 189–191$^{b)}$ |

TABLE 10-continued

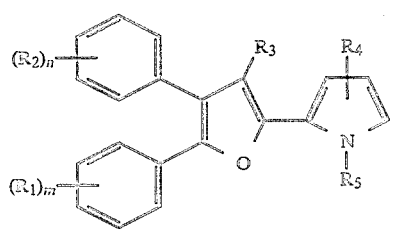

(I)

| Comp. No. | $(R_1)_m$ | $(R_2)_n$ | $R_3$ | $R_4$ | $R_5$ | m.p. (°C.) |
|---|---|---|---|---|---|---|
| 166 | 4-F | 4-OCH$_3$ | H | 5-C$_2$H$_5$ | CH$_2$CO$_2$H | 183–186 |
| 167 | 4-Cl | 4-OCH$_3$ | H | 5-C$_2$H$_5$ | CH$_2$CO$_2$H | 193–197 |
| 168 | 4-OCH$_3$ | 4-F | H | 5-C$_2$H$_5$ | CH$_2$CO$_2$H | 202–205 |
| 169 | 4-OCH$_3$ | 4-Cl | H | H | CH$_2$CO$_2$H | 197–199 |
| 170 | 4-OCH$_3$ | 4-Cl | H | 5-CH$_3$ | CH$_2$CO$_2$H | 201–204 |
| 171 | 4-OCH$_3$ | 4-Cl | H | 5-C$_2$H$_5$ | CH$_2$CO$_2$H | 199–202 |
| 172 | 4-OCH$_3$ | 4-Cl | H | 5-COCH$_3$ | H | 232–235 |
| 173 | 2-OCH$_3$ | 2-OCH$_3$ | H | H | CH$_2$CO$_2$H | 200 |
| 174 | 3-OCH$_3$ | 3-OCH$_3$ | H | H | CH$_2$CO$_2$H | 173–175c) |
| 175 | 4-OCH$_3$ | 4-OCH$_3$ | H | H | CH$_2$CO$_2$H | 204 |
| 176 | 4-OCH$_3$ | 4-OCH$_3$ | H | H | CH(CH$_3$)CO$_2$H | 149–153 |
| 177 | 4-OCH$_3$ | 4-OCH$_3$ | H | H | CH$_2$CH$_2$CO$_2$Et | 59–60 |
| 178 | 4-OCH$_3$ | 4-OCH$_3$ | H | H | CH$_2$CH$_2$CO$_2$H | 162–164 |
| 179 | 4-OCH$_3$ | 4-OCH$_3$ | H | H | CH$_2$CN | 94–96 |
| 180 | 4-OCH$_3$ | 4-OCH$_3$ | H | H | CH$_2$CH$_2$OEt | 51–53 |
| 181 | 4-OCH$_3$ | 4-OCH$_3$ | CH$_3$ | H | SO$_2$Ph | 116–118 |
| 182 | 4-OCH$_3$ | 4-OCH$_3$ | CH$_3$ | H | H | 144–145 |
| 183 | 4-OCH$_3$ | 4-OCH$_3$ | CH$_3$ | H | CH$_2$CO$_2$Et | 121–122 |
| 184 | 4-OCH$_3$ | 4-OCH$_3$ | CH$_3$ | H | CH$_2$CO$_2$H | 215 |
| 185 | 4-OCH$_3$ | 4-OCH$_3$ | H | 4-C$_2$H$_5$ | CH$_2$CO$_2$H | 167–168 |
| 186 | 4-OCH$_3$ | 4-OCH$_3$ | H | 4-CH(CH$_3$)$_2$ | SO$_2$Ph | 148–150 |
| 187 | 4-OCH$_3$ | 4-OCH$_3$ | H | 4-CH(CH$_3$)$_2$ | H | 192–194 |
| 188 | 4-OCH$_3$ | 4-OCH$_3$ | H | 4-CH(CH$_3$)$_2$ | CH$_2$CO$_2$H | 171–173 |
| 189 | 4-OCH$_3$ | 4-OCH$_3$ | H | 4-C(CH$_3$)$_3$ | SO$_2$Ph | 173–176 |
| 190 | 4-OCH$_3$ | 4-OCH$_3$ | H | 4-C(CH$_3$)$_3$ | CH$_2$CO$_2$H | 195–198 |
| 191 | 4-OCH$_3$ | 4-OCH$_3$ | H | 5-CH$_3$ | CH$_2$CO$_2$Et | 102–104 |
| 192 | 4-OCH$_3$ | 4-OCH$_3$ | H | 5-CH$_3$ | CH$_2$CO$_2$H | 211–214 |
| 193 | 4-OCH$_3$ | 4-OCH$_3$ | H | 5-C$_2$H$_5$ | CH$_2$CO$_2$Et | 98–100 |
| 194 | 4-OCH$_3$ | 4-OCH$_3$ | H | 5-n-C$_3$H$_7$ | CH$_2$CO$_2$Et | 84–87 |
| 195 | 4-OCH$_3$ | 4-OCH$_3$ | H | 5-n-C$_3$H$_7$ | CH$_2$CO$_2$H | 171–173 |
| 196 | 4-OCH$_3$ | 4-OCH$_3$ | H | 5-CHO | H | 189–191 |
| 197 | 4-OCH$_3$ | 4-OCH$_3$ | H | 5-CHO | CH$_2$CO$_2$Et | 120–122 |
| 198 | 4-OCH$_3$ | 4-OCH$_3$ | H | 5-CHO | CH$_2$CO$_2$H | 194–196 |
| 199 | 4-OCH$_3$ | 4-OCH$_3$ | H | 5-COCH$_3$ | CH$_2$CO$_2$Et | 121–123 |
| 200 | 4-OCH$_3$ | 4-OCH$_3$ | H | 5-COCH$_3$ | CH$_2$CO$_2$H | 198–200 |
| 201 | 4-OCH$_3$ | 4-OCH$_3$ | H | 5-COC$_2$H$_5$ | H | 180–183 |
| 202 | 4-OCH$_3$ | 4-OCH$_3$ | H | 5-COC$_2$H$_5$ | CH$_2$CO$_2$H | 169–172 |
| 203 | 4-OCH$_3$ | 3,4-(OCH$_3$)$_2$ | H | H | CH$_2$CO$_2$H | 168–170 |
| 204 | 4-OCH$_3$ | 3,4-(OCH$_3$)$_2$ | H | 5-C$_2$H$_5$ | CH$_2$CO$_2$H | 150–152 |
| 205 | 2,4-(OCH$_3$)$_2$ | 4-OCH$_3$ | H | H | CH$_2$CO$_2$H | 197c) |
| 206 | 2,4-(OCH$_3$)$_2$ | 4-OCH$_3$ | H | H | CH$_2$CO$_2$H | 190–193 |
| 207 | 2,3,4-(OCH$_3$)$_3$ | 4-OCH$_3$ | H | H | CH$_2$CO$_2$H | 144–145 |
| 208 | 4-OCH$_3$ | 4-OC$_2$H$_5$ | H | H | CH$_2$CO$_2$H | 185–188 |
| 209 | 4-OCH$_3$ | 4-OC$_2$H$_5$ | H | 5-C$_2$H$_5$ | CH$_2$CO$_2$H | 190–193 |
| 210 | 4-OC$_2$H$_5$ | 4-OCH$_3$ | H | H | CH$_2$CO$_2$H | 182–184 |
| 211 | 4-OC$_2$H$_5$ | 4-OCH$_3$ | H | 5-C$_2$H$_5$ | CH$_2$CO$_2$H | 195–198 |
| 212 | 4-OC$_2$H$_5$ | 4-OC$_2$H$_5$ | H | H | CH$_2$CO$_2$Et | 94–97 |
| 213 | 4-OC$_2$H$_5$ | 4-OC$_2$H$_5$ | H | H | CH$_2$CO$_2$H | 144–146 |
| 214 | 4-OC$_2$H$_5$ | 4-OC$_2$H$_5$ | H | 5-CH$_3$ | CH$_2$CO$_2$Et | 84–86 |
| 215 | 4-OC$_2$H$_5$ | 4-OC$_2$H$_5$ | H | 5-CH$_3$ | CH$_2$CO$_2$H | 233–235 |
| 216 | 4-OC$_2$H$_5$ | 4-OC$_2$H$_5$ | H | 5-C$_2$H$_5$ | CH$_2$CO$_2$Et | 74–76 |
| 217 | 4-OC$_2$H$_5$ | 4-OC$_2$H$_5$ | H | 5-C$_2$H$_5$ | CH$_2$CO$_2$H | 213–216 |
| 218 | 4-OC$_2$H$_5$ | 4-OC$_2$H$_5$ | H | 5-CHO | H | 176–178 |
| 219 | 4-OC$_2$H$_5$ | 4-OC$_2$H$_5$ | H | 5-COCH$_3$ | H | 185–186 |
| 220 | 4-SCH$_3$ | 4-OCH$_3$ | H | H | CH$_2$CO$_2$H | 200 |
| 221 | 4-SOCH$_3$ | 4-OCH$_3$ | H | H | CH$_2$CO$_2$H | 220 | a)diethylamine salt,
b)containing 1 molecule of ethanol,
c)dicyclohexylamine salt Examples of the pharmaceutical composition comprising the compound of the present invention represented by formula (I) are described below. However, the pharmaceutical compositions containing the compounds of the present invention are not limited to these examples.

| Formulation 1 | |
|---|---|
| Component | Amount in one tablet (mg) |
| Active ingredient | 150 |
| Lactose | 113 |

-continued

Formulation 1

| Component | Amount in one tablet (mg) |
| --- | --- |
| Corn starch | 20 |
| Crystalline cellulose | 15 |
| Magnesium stearate | 2 |

The above components were mixed and pressed to form a tablet.

Formulation 2

| Component | Amount in one capsule (mg) |
| --- | --- |
| Active ingredient | 100 |
| Lactose | 110 |
| Corn starch | 48 |
| Magnesium stearate | 2 |

The above components were mixed and filled into a capsule (No. 2).

Formulation 3
Granules of the following composition were prepared.

| Component | |
| --- | --- |
| Active ingredient | 100 mg |
| Lactose | 840 mg |
| D-mannitol | 800 mg |
| Crystalline cellulose | 200 mg |
| Hydroxypropylcellulose | 60 mg |

Drug Formulation 4
Syrup of the following composition was prepared.

| Component | |
| --- | --- |
| Active ingredient | 1 g |
| White sugar | 150 g |
| D-Sorbitol solution (70%) | 125 g |
| Methyl p-hydroxybenzoate | 200 mg |
| Propyl p-hydroxybenzoate | 100 mg |
| Sodium citrate | 5 g |
| Citric acid | 800 mg |
| Lemon Oil | 1 g |
| Purified water | balance |
| Total | 500 ml |

Drug Formulation 5
Injection of the following composition (pH 7) was prepared.

| Component | |
| --- | --- |
| Active ingredient | 15 mg |
| Sodium chloride | suitable amount |
| 1N Hydrochloric acid | suitable amount |
| 1N Potassium hydroxide | suitable amount |
| Potassium dihydrogenphosphate | suitable amount |
| Distilled water for injection | balance |
| Total | 1 ml |

Drug Formulation 6

| Component | |
| --- | --- |
| Active ingredient | 1 g |
| Glycerin ester of aliphatic acid | 99 g |

The above components were homogenized with warming and cast into a metal mold to solidify by cooling, and a suppository was taken out from the mold.

What is claimed is:

1. A diphenylpyrrolylfuran derivative represented by the following formula (I):

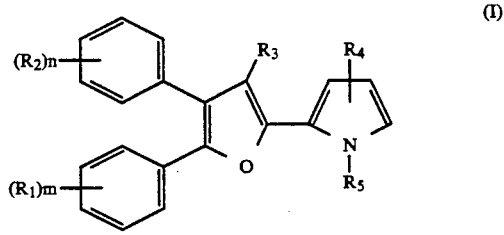

wherein
$R_1$ and $R_2$ may be the same or different and independently represent a hydrogen atom, a halogen atom, a lower alkyl group, a lower alkoxy group, a lower alkylthio group, or a lower alkylsulfenyl group;
m and n independently represent an integer of from 1 to 3;
$R_3$ represents a hydrogen atom or a lower alkyl group,
$R_4$ represents a hydrogen atom, a lower alkyl group, or a lower acyl group; and
$R_5$ represents a hydrogen atom, a lower alkyl group which may have one or more suitable substituents, a lower alkoxy- or an aryloxy-carbonyl group, an acyl group, or a sulfonyl group, and pharmaceutically acceptable salts thereof.

2. A pharmaceutical composition comprising a diphenylpyrrolylfuran derivative represented by the following formula (I):

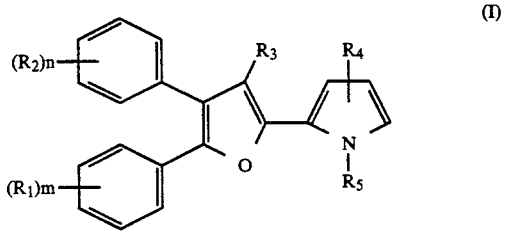

wherein
$R_1$ and $R_2$ may be the same or different and independently represent a hydrogen atom, a halogen atom, a lower alkyl group, a lower alkoxy group, a lower alkylthio group, or a lower alkylsulfenyl group;
m and n independently represent an integer of from 1 to 3;
$R_3$ represents a hydrogen atom or a lower alkyl group,
$R_4$ represents a hydrogen atom, a lower alkyl group, or a lower acyl group; and
$R_5$ represents a hydrogen atom, a lower alkyl group which may have one or more suitable substituents, a lower alkoxy- or an aryloxy-carbonyl group, an acyl group, or a sulfonyl group, or pharmaceutically acceptable salt thereof.

3. The pharmaceutical composition according to claim 2 which is useful for a preventive or therapeutic treatment of inflammatory disease.

4. The pharmaceutical composition according to claim 2 which is useful for a preventive or therapeutic treatment of allergic diseases.

5. The pharmaceutical composition according to claim 2 which is useful as a platelet aggregation inhibitor.

* * * * *